(12) United States Patent
Tashayyod et al.

(10) Patent No.: US 10,880,488 B2
(45) Date of Patent: Dec. 29, 2020

(54) RAPID REAL-TIME LARGE DEPTH OF FIELD, WHOLE BODY, MULTI-SPECTRAL OPTICAL IMAGING FOR SKIN SURVEILLANCE AND PHOTOGRAPHY

(71) Applicant: PARTO INC., Potomac, MD (US)

(72) Inventors: Davood Tashayyod, Potomac, MD (US); Rauni Edward Lindross, Dundalk, MD (US); Bahar Dasgeb, Philadelphia, PA (US)

(73) Assignee: PARTO INC., Potomoc, MD (US)

( * ) Notice: Subject to any disclaimer, the term of this patent is extended or adjusted under 35 U.S.C. 154(b) by 72 days.

(21) Appl. No.: 16/264,300

(22) Filed: Jan. 31, 2019

(65) Prior Publication Data

US 2019/0166312 A1 May 30, 2019

Related U.S. Application Data

(63) Continuation-in-part of application No. PCT/US2017/045154, filed on Aug. 2, 2017.
(Continued)

(51) Int. Cl.
*H04N 5/247* (2006.01)
*H04N 5/232* (2006.01)
(Continued)

(52) U.S. Cl.
CPC ....... *H04N 5/23299* (2018.08); *A61B 5/0064* (2013.01); *A61B 5/0073* (2013.01); *A61B 5/0077* (2013.01); *A61B 5/444* (2013.01); *G06T 7/0016* (2013.01); *H04N 5/2253* (2013.01); *H04N 5/2256* (2013.01); *H04N 5/23232* (2013.01); *H04N 5/247* (2013.01); *G06T 2207/30096* (2013.01)

(58) Field of Classification Search
CPC .. H04N 5/23299; H04N 5/225; H04N 5/2256; H04N 5/23232; H04N 5/247; A61B 5/0064; A61B 5/0073; A61B 5/0077; A61B 5/444; G06T 7/0016
USPC .......................................................... 348/77
See application file for complete search history.

(56) References Cited

U.S. PATENT DOCUMENTS 10,122,997 B1 * 11/2018 Sheffield .............. H04N 13/282
2002/0177885 A1   11/2002 Eisfeld et al.
(Continued)

FOREIGN PATENT DOCUMENTS

WO        2009070160 A1    6/2009

OTHER PUBLICATIONS

Supplementary European Search Report issued in corresponding European Application No. EP17837626.5 dated Jan. 2, 2020.

*Primary Examiner* — Nguyen T Truong
(74) *Attorney, Agent, or Firm* — Cozen O'Connor (57) ABSTRACT

Systems and methods for generating high resolution 3D images of the entire human skin comprising at least two sets of cameras, a first set being sensitive to UV light while the second set being sensitive to visible frequencies of light, wherein subsets of each camera set are focused at different focal distances; wherein the system provides a rotatable structure wherein the two sets of cameras are mounted adjacent to the source of light; wherein the rotatable structure is engaged to a program that can define the point of rotation, so as to allow for a reproducible mechanism to take images along the path of rotation.

5 Claims, 9 Drawing Sheets

Related U.S. Application Data

(60) Provisional application No. 62/370,039, filed on Aug. 2, 2016.

(51) Int. Cl.
*A61B 5/00* (2006.01)
*G06T 7/00* (2017.01)
*H04N 5/225* (2006.01)

(56) References Cited

U.S. PATENT DOCUMENTS

| | | |
|---|---|---|
| 2004/0042685 A1 | 3/2004 | Zhou et al. |
| 2006/0085053 A1 | 4/2006 | Anderson et al. |
| 2006/0258942 A1 | 11/2006 | Van Beek et al. |
| 2008/0021275 A1 | 1/2008 | Tearney et al. |
| 2008/0194968 A1 | 8/2008 | Drugge |
| 2009/0118600 A1 | 5/2009 | Ortiz et al. |
| 2014/0005555 A1 | 1/2014 | Tesar |
| 2014/0015951 A1 | 1/2014 | Millikan |
| 2016/0035108 A1 | 2/2016 | Yu et al. |

\* cited by examiner

RAPID REAL-TIME LARGE DEPTH OF FIELD, WHOLE BODY, MULTI-SPECTRAL OPTICAL IMAGING FOR SKIN SURVEILLANCE AND PHOTOGRAPHY

PRIORITY CLAIM

This application is a continuation-in-part of International Phase patent application Serial No. PCT/US17/45154 which was filed with the U.S. Patent and Trademark Office on Aug. 2, 2017. This application claims benefit under 35 U.S.C. § 119(e) of U.S. Provisional Application No. 62/370,039 filed Aug. 2, 2016, the contents of which are incorporated herein by reference in its entirety.

FIELD OF INVENTION

The present application is generally related to rapidly, accurately and reproducibly imaging the entire surface of the human body.

BACKGROUND OF THE INVENTION

World-wide, there has been an alarming rise in skin cancer—the most common malignancy in humans—over the past several decades including a persistent rise in the incidence of both melanoma and other skin cancers and a trend towards a younger age at diagnosis. It is estimated that every year, 3.5 million new non-melanoma skin cancers and 74,000 new melanoma cases are diagnosed and treated in the United States alone. This is greater than the incidence of all other cancers combined.

Even melanoma, the deadliest skin cancer, can be cured if detected early. A feasible and accurate method is critical in early detection of skin malignancies—when they are curable—and prevention of further morbidity and mortality associated with advanced skin cancer and adverse event associated with their treatment.

Non-automated photography is presently used to attempt to capture progression of disease. Such photography entails manually shooting and one by one examination of the 27 or so images. In addition, the procedure needs a dedicated space and photographer. Such system is time consuming, inefficient and costly. In addition, the aforementioned 27 or so images only document the visible light domain without color fidelity. Moreover, this approach does not allow for automated computed numerical analysis because of inconsistent image gathering, different light and focal angles, among other issues.

One of the more significant attempts at automation has been by DermSpectra (www.Dermspectra.com). While this system provides automated photography, the non-3D user interface is still time consuming and non-intuitive for the clinicians. It does not provide color fidelity and is not ideal for numerical analysis. Additionally, no available system in the market, including DermSpectra, provides UV (Wood's lamp) images which is very important in better assessment of pigmented lesions.

Another know system which has been co-developed by Memorial Sloan Kettering Cancer Center and Canfield is "Vectra 360". The Vectra system lacks color fidelity, UV domain imaging and depth of field necessary for optimal imaging of the skin legions. The Vectra system also requires a large dedicated space and is very expensive. Moreover, the limited data sets caused by limited angles of views and number of spectra handicaps the existing systems when it comes to numerical analysis of lesions.

SUMMARY OF THE INVENTION

The invention and embodiments described herein are related to image capturing devices, systems, and methods of taking photographs of and treating persons with said devices. In a preferred embodiment, the invention is a device used to capture a large number of ultra-high resolution and ultra large depth of field images of the entire body from different angles in a very short duration while restricting the footprint of the entire device to around 8' in diameter. The device particularly utilizes two or three sets of cameras. In the case of the system with two sets of cameras, one in the UV spectrum and another in the visible light spectrum, wherein each set contains two camera sub-sets, each subset having a different focal distance. Wherein the device comprises components to rotate around a cylindrical or half cylindrical feature, so as to capture a body positioned within the cylinder in a 180 or 360 degree image.

An embodiment of the invention provides a system for generating high resolution 3D images comprising multiple sets of cameras that are sensitive to different bands of light frequencies, wherein sub sets of cameras that are sensitive to a band of light frequencies are cameras that are focused at a different focal distances; wherein the system provides a rotatable structure wherein the multiple sets of cameras are mounted in an arc around the subject at specific annular increments while the cameras are flanked by at least one bank of light sources; wherein the rotatable structure is engaged to a software program that can define the point of rotation, so as to allow for a reproducible mechanism that rotates the structure by the same annular increments to take images of different light sensitivities and different focal distances but from a singular point of view.

A further embodiment is directed to a system comprising multiple sets of cameras utilized for each wavelength range of interest. For simplicity, a one wavelength range with 2 focal distance camera set configuration is described herein. In practice, more than two focal distances may be necessary for cameras with larger sensor sizes (larger than APS-C). The cameras in the first focal distance (e.g. 5 cameras) will be placed along a line parallel to the center line of an imaginary cylinder surrounding the subject (e.g. a cylinder with 4' base radius and 10' height). Each of the cameras at the first focal distance is placed to cover a portion of the person's body (e.g. one camera for lower leg, one for upper leg, one for lower torso, one for upper torso and one for head). The cameras in the second focal distance (another 5 cameras) will be placed similarly along another imaginary line parallel to the center line but in a different angular position relative to the first set (e.g. the camera sits 6 degrees apart). All the cameras in the first focal distance are focused on a plane of focus outside but near the edge of the smallest imaginary circle that can completely encircle the subject. The cameras in the second focal distance are focused on a plane of focus inside but near the edge of the largest imaginary circle that can completely encircle the subject. All the cameras in the first focal distance and second focal distance are triggered simultaneously when the device structure rotates to the right position along its movement. The structure will then turn around the person being scanned by a specific increment (e.g. 6 degrees) at a time and more images are captured until every camera set fully rotates around the patient by 180 or 360 degrees. After the person is completely imaged in all the regions of the body, the images from the cameras at the first focal distance are stitched together to create an ultra-high resolution image of the closer focus plane while the images in the second focal distance when stitched together create a second ultra-high resolution image of the second focus plane. The further plane (further from camera) images from the first camera set at time increments x and closer plane images from the second camera set at time increment x+1 are then stacked together with a photo stacking algorithm thereby yielding one ultra-high resolution image with a very wide depth of filed in a very small fraction of the image acquisition time that is necessary for traditional focus stacking methods.

Another embodiment of the invention comprises one set of cameras that contain multiple linear sensor arrays (as opposed to rectangular sensors) placed side by side with each subset of sensors sensitive to different bands of light frequencies (FIG. 9), wherein the lens system for the camera is installed at a tilt angle relative to the plane of sensors such that each of the sensor arrays are focused at a different focal distances; wherein the system provides a rotatable structure wherein the multiple multi-sensor cameras are mounted in a line parallel to the center line of an imaginary cylinder around the subject while the cameras are flanked by at least one bank of light sources; wherein the rotatable structure is engaged to a software program that can define the point of rotation, so as to allow for a reproducible mechanism that rotates the structure by the same annular increments to take images of different light sensitivities and different focal distances but from a singular point of view.

Another embodiment of the invention is comprised of one set of cameras that contain a single rectangular sensor with strips of light filters (FIG. 10) passing specific bands of light frequencies placed side by side with each on the one rectangular sensors, wherein the lens system for the camera is installed at a tilt angle relative to the plane of sensors such that stripe like groups of pixels within the same sensor are focused at a different focal distance; wherein the system provides a rotatable structure wherein the multiple sets of cameras are mounted in a line parallel to the center line of an imaginary cylinder around the subject while the cameras are flanked by at least one bank of light sources; wherein the rotatable structure is engaged to a software program that can define the point of rotation, so as to allow for a reproducible mechanism that rotates the structure by the same annular increments to take images of different light sensitivities and different focal distance but from a singular point of view.

A further embodiment of this invention comprises of similar components but with light sources being capable of producing large quantities of light within the UV spectrum so that it can also be used as a UVA/UVB Phototherapy unit A further embodiment is directed towards a system for generating high resolution 3D images comprising two sets of cameras, a first set being sensitive to UV light while the second set being sensitive to visible frequencies of light, wherein sub sets of the visible light sensitive cameras are set focused at different focal distances; wherein the system provides a rotatable structure wherein the two sets of cameras are mounted adjacent to at least one bank of light; wherein the rotatable structure is engaged to a program that defines the point of rotation, so as to allow for a reproducible mechanism to take images at predetermined points along a path of rotation. In certain embodiments, the system further comprising a base, having a quartz plate bottom, and a camera positioned underneath the quartz plate bottom, wherein the camera takes an image in at least one of UV or visible light. In further embodiments, the rotatable structure is engaged to a carriage comprising at least one pinion gear, and a track defining a circular structure having evenly spaced notches for engaging a pinion gear; wherein the pinion gear and track allow for defined movements along the path of rotation. In preferred embodiments, said notches are spaced at 0.5 degrees apart.

In preferred embodiments, systems of the present disclosure comprise ten total cameras, five cameras in the UV light and five in the visible light, wherein the sub sets of visible light sensitive cameras comprise at least two cameras at a first focus distance and at least two cameras at a second focus distance. Certain embodiments, further comprise a UVA/UVB Phototherapy unit capable of generating a metered dose of UVA/UVB using the circular track features of the device.

In a further embodiment, an imaging device comprising a circular track structure having a plurality of evenly spaced notches, a carriage, having at least one pinion gear corresponding to the evenly spaced notches, a motor to drive a pinion gear, a frame mounted to the carriage, and a light tree, comprising at least one light and a plurality of cameras; said plurality of cameras comprise at least two groups, with a first group of cameras having a different light frequency sensitivities as to the second group of cameras; and at least one of the groups of cameras having a different focus distance from at least one other camera in said group; a light source generating a light intensity in a predetermined range and with a color temperate within a predetermined range; and software run on a computer in electronic communication with the at last two groups of cameras and the motor; wherein the device can be utilized to provide 3D images of the skin of a subject to allow for detection of skin cancers at early stages when they are still curable. In a preferred embodiment, the first group of cameras is a visible light camera and wherein the second group of cameras are UV cameras. Preferentially, the evenly spaced notches are separated by between 2 and 0.1 degrees.

A further embodiment is directed towards a method for visualizing a subject's anatomical features, comprising: taking a first image of a subject utilizing a 3D imaging device wherein said 3D imaging device comprises: a first camera set being sensitive to UV spectra, and a second camera set being sensitive to visible light, wherein the second camera set being sensitive to visible light comprises at least one camera focused at a first focal distance and at least a second camera focused at a second, different focal distance; rotating the first and second camera sets around a rotatable structure wherein the two sets of cameras are mounted adjacent to at least one bank of light; wherein the rotatable structure is engaged to a program that can define the point of rotation, so as to allow for a reproducible mechanism to take images along the path of rotation; taking a second image of said same person at a second time. In certain embodiments, a further step comprises comparing the first and second images to assess progression of said skin disease or disorder; wherein a difference between said first and second images defines the progression or regression of the skin disease or disorder.

A further embodiment is directed towards a method for treating a skin disease or disorder susceptible to UVA or UVB light comprising: administering to said patient a dose of UVA or UVB light, said dose provided by a device mounted on a rotatable structure comprising a circular track structure having a plurality of evenly spaced notches, a carriage, having at least one pinion gear corresponding to the evenly spaced notches, a motor to drive a pinion gear, a frame mounted to the carriage, and a light tree, comprising at least one light and a plurality of cameras; said plurality of cameras comprise at least two groups, with a first group of cameras having a different light frequency sensitivities as to the second group of cameras; and at least one of the groups of cameras having a different focus distance from at least one other camera in said group; a light source generating a light intensity in a predetermined range and with a color temperate within a predetermined range; and software run on a computer in electronic communication with the at last two groups of cameras and the motor; wherein the device can be utilized to provide 3D images of the skin of a subject to allow for detection of skin cancers at early stages when they are still curable; wherein the light tree is programmed to provide a sufficient does of UVA or UVB to a patient, and the device rotates around the track to provide metered doses along a predetermined treatment path.

An further embodiment is directed towards an imaging device comprising two sets of cameras, a first set being sensitive to UV spectra while the second being sensitive to visible light, wherein sub sets are each focused at different focal distances; wherein the device provides a rotatable structure wherein the two sets of cameras are mounted adjacent to at least one bank of light; wherein the rotatable structure is engaged to a program that can define the point of rotation, so as to allow for a reproducible mechanism to take images along the path of rotation.

A further embodiment is directed towards an imaging device comprising a camera positioned on a movable boom, wherein said camera comprises six line-scan sensors aligned parallel to one another, with three sets of two sensors having filters for one the three spectra of interest providing two line-scan sensors having UV pass filters, two sensors having IR pass filters and the last two filters having visible pass filter; the camera comprising a lens, oriented at a tilt angle between 0 and 90 degrees, with respect to sensor plane, wherein the plane of focus will be at a tilt angle with the plane of sensors; and wherein the angle of the tilt will be selected such that the furthest part of the plane of focus is at the same distance as the further part of a typical subject's body from the camera and the closed part of the plane of focus is at the same distance as the nearest part of a typical subject's body wherein each lines can sensors will be focused at a different focal distance due to the tilt of the lens. The device, wherein said movable boom is a curved boom, traveling at least 90 degrees from a first point to a second point. In further embodiments, wherein said movable boom is a curved boom, traveling at least 180 degrees from a first point to a second point, or 360 degrees around said curved boom.

A further embodiment is directed towards a method of capturing an image from a patient comprising: taking a set of images from a camera, said camera positioned on a movable boom, wherein said camera comprises six line-scan sensors aligned parallel to one another, with three sets of two sensors having filters for one the three spectra of interest providing two line-scan sensors having UV pass filters, two sensors having IR pass filters and the last two filters having visible pass filter; the camera comprising a lens, oriented at a tilt angle between 0 and 90 degrees, with respect to sensor plane, wherein the plane of focus will be at a tilt angle with the plane of sensors; and wherein the angle of the tilt will be selected such that the farthest part of the plane of focus is at the same distance as the farther part of a typical subject's body from the camera and the closed part of the plane of focus is at the same distance as the nearest part of a typical subject's body wherein each lines can sensors will be focused at a different focal distance due to the tilt of the lens; stacking the resulting set of images to stack two visible images, two UV images, and two IR images; generating a high depth of field visible image, a high depth of field UV image, and a high depth of field IR image from the stacked images. In certain embodiments, said movable boom rotates around a patient from between 90 to 360 degrees to capture several sets of images. In certain embodiments, images are captured between every 1 and 15 degrees around the rotation of the boom.

In further embodiments, an imaging device, comprising 30 cameras oriented around on a mechanical boom, the 30 cameras are oriented into five sets of six cameras, with each of the sets oriented on a different portion of said mechanical boom; each of the set of six cameras comprises two cameras having a filter to capture UV, two to capture IR, and two to capture images in the visible spectra; each set of six cameras is further defined so that one UV, one IR, and one visible spectra camera is oriented to capture an image at a first focal distance; and the second of UV, IR, and visible spectra in each set are oriented to capture an image at a second focal distance. In certain embodiments, the five sets of six cameras are oriented on said mechanical boom aligned in linear fashion with each set spaced apart by between 8 and 15 inches. In certain embodiments, the spacing of the five sets is defined based on a patient, where one set will cover the head, one set will cover the upper torso, one set for lower torso, one set upper legs, and the last set for lower leg.

In accordance with one embodiment, a system is provided for generating wide depth of field and high resolution images comprising: two sets of cameras comprising a first camera set and a second camera set; a rotatable structure to which the first camera set and the second camera set are mounted for rotating the two sets of cameras around a subject, to produce wide depth of field of images in a high speed manner; wherein the first set of camera are focused at the first focus distance and the second set of camera are focused at a second focus distance, the cameras being mounted adjacent to at least one illumination source; wherein the rotatable structure is controlled by a program that defines a movement profile along a path of rotation, wherein the program moves the first and second sets of cameras around the subject, stops to specific angles of view and obtains images from all the cameras at each stop; wherein a subsequent incremental move of the structure will place the second set of cameras at the same angle of view of the subject as the set of first cameras in the next time increment; wherein after a set number movements, a full rotation of the structure around the subject is completed; wherein the images from the first set of cameras at time increment x are stitched together; wherein the images from the second sets of camera at time increment x+1 are stitched together; and wherein the resulting image from the stitching operations from the first set of cameras at time increment x and resulting image from stitching operations from the second set of cameras at time increment x+1 are stacked together to create very high resolution and large depth of field image from one angle of view. By repeating the same process for images obtained at the other angles of views along the path of rotation, the system can produce a plurality of wide depth of field and high resolutions images from all angles of views along a path of rotation.

In accordance with another embodiment, a method of utilizing the multitude of images is disclosed to track and classify a lesion on a subject. The method comprises the steps of: determining the actual size of a lesion by utilizing the known positions of the cameras along the path of movement and the known angle of the cameras along the path of movement; detecting the boundary of a lesion by computing the boundary multiple times from multiple images of the same lesion and then, depending on the mode of device, finding the average of the boundaries in diagnostics mode or the union of the resulting boundaries in the screening mode; tracking the position of a lesion, by utilizing the actual distances between a lesion and nearby lesions, as well as the actual distances between the lesion and certain body landmarks, such as such as the navel, the tip of the nose, the tips of the middle fingers, the tips of the big toes, the points of the shoulder, the points of the elbows and the points of the ankles; and classifying the lesion by machine learning based on multiple images of the same lesion

DETAILED DESCRIPTION OF THE EMBODIMENTS

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the claims.

As used herein, terms such as "a," "an," and "the" include singular and plural referents unless the context clearly demands otherwise.

As used herein, the term "about" means within 10% of a stated number.

As used herein, the term "body landmarks" includes body reference points such as the navel, the tip of the nose, the tips of the middle fingers, the tips of the big toes, the points of the shoulder, the points of the elbows and the points of the ankles.

An objective and reproducible whole-body screening method is needed to fill the current gap in systematic standardized population screening and surveillance in regards to skin malignancies, particularly in high-risk persons, such a system will enable clinicians or a software algorithm or a combination of the two to accurately monitor the subjects over time to document any changes in previously identified lesions or to detect new lesions rapidly at the point of care. Additionally, whole body scanning can be applied to survey and follow up treatment response for any other skin condition including inflammatory, traumatic, autoimmune or cosmetic and assess precise therapeutic response of individual subject.

Such a system is capable of reproducing high spatial, contrast, and temporal resolution, accurate pictures of the whole-body surface of human skin can be used to provide dermatologic care to any hospital, clinic or underserved areas where onsite dermatologist is not available.

Such a system can also be used to provide Forensic clinicians with clinical and pathology documentation of injuries for evidence in court in assaults, Blunt force (punch, kick, blunt weapons), Sharp force (stab, cut), Firearm (gunshot wounds, shotgun wounds), Rape and domestic assault, Child abuse and Elder Abuse cases.

Herein, we describe a multi-spectra system, while low in cost, will keep the entire body in focus and capture images at a much higher speed than competing systems. Most importantly, the intuitive 3D user interface will significantly reduce operator time and allow for repeated image capturing at time 1 and time x, to detail disease progression. As taken in a consistent manner, such systems allow for automated comparisons, which is not possible in prior technologies.

The system is a relatively compact device (relative to exiting devices e.g. Canfield Scientific's Vectra 3D device) that can survey the full body surface deeper and with higher resolution, larger depth of field, and with multiple spectra (e.g. capable of producing visible, IR and UV renditions), heretofore impossible with prior technologies. Additionally, the system's multitude of angles of views provides much more data than existing devices, allowing for much improved determination of lesion features and thereby better lesion classification.

Maximizing the depth of field problem in close proximity is one of the biggest challenges in photography. The reason being that with the small (under 0.25") sensor cameras when stopped down could potentially provide enough depth of field. However, at the current state of technology, the amount of light available to the sensor (when the camera's aperture is stopped down for large depth of filed and the shutter speed sped up enough to image the whole body from many angles in a reasonable time) is not enough to produce high quality and clinically relevant images; with larger sensor cameras, at apertures that are large enough not to diminish image quality due to diffraction, the depth of field is not sufficiently large to keep all the features of a larger human body in focus at close camera/body proximity.

Below is described several embodiments, each providing a solution to the depth of field problem. These embodiments may be utilized alone, or combined together to create systems and devices for taking high quality images to allow for diagnosis and monitoring of patient modification through disease progression.

The first embodiment depicts an accelerated version of a known slow focus stacking method. In the second embodiment instead of high-speed stacking, the disclosed embodiment uses very small sensors to create the necessary large depth of field. The second embodiment will become more important in future as the small sensors that have the necessary sensitivity and dynamic range characteristics become available (prodded by cell phone industry).

In certain preferred embodiments, it is envisioned to combine the first and second embodiments to generate both the advantages of stacking images with the features of use smaller sensors to provide greater depth of field.

Multiple planes of focus: In one embodiment, through the use of a multiple cameras with small imaging sensors (APS-C or smaller), with each group of cameras focused at a different plane of focus. For example, a set of ten small-sensored cameras may be utilized, with two groups of five cameras. Each group of cameras would be focused at different focal distance. In this method all the images from a plurality of angles, preferably 60 or more angles of view are captured very rapidly while the subject is a standing pose in center of the device and the robotics structure is rapidly making one full revolution around the subject. Then after the subject leaves the device (off-line) for each angle of view, the five images that are focused on the same plane are first stitched together to create two high resolution images (one for each plane of focus). The cameras are directed with parallel axis of views and two stitched images are cropped so that they both contain the same information in order to eliminate all effects of parallax. Then those two high resolution images will be fused together with the help of the focus stacking software (or alternatively through the use of cameras feature the built-in focus stack feature), which will combine the highest contrast areas (the best focused portion) from each of the two high resolution pictures resulting into 60 or more high resolution and large depth of field 2D image (one image per angle of view). When viewed in sequence the clinician can in effect see a 3D rendering with very high resolution and high depth of field. The system will thereby provide a very natural user interface to the clinician who will have the ability to rotate, zoom and pan two such 3D renderings (previous scan vs latest scan or visible scan vs UV scan) simultaneously.

Figure 1:
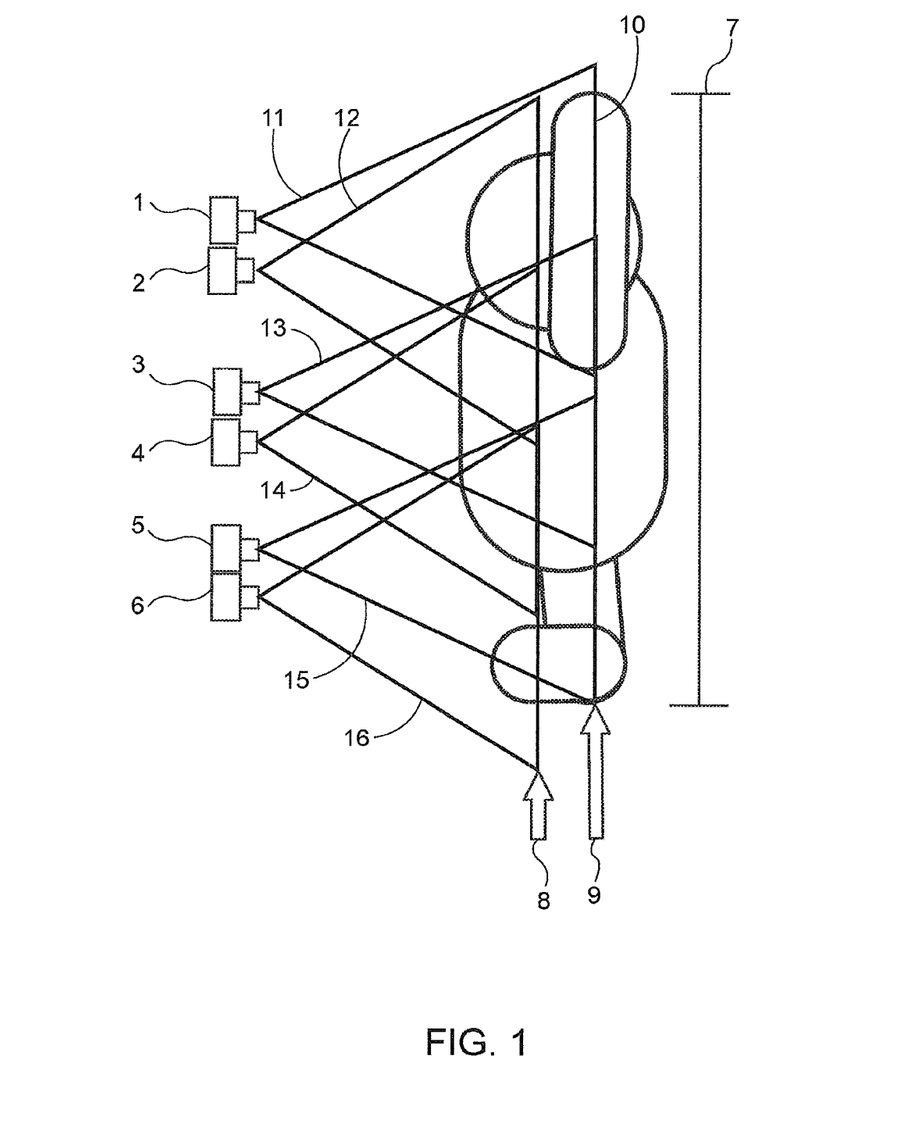
FIG. 1 is a schematic representation of a scanning device.

For example, in FIG. 1, there are depicted six cameras, numbered 1-6, with two different focal planes (meaning different cameras are using a different focus distance to create a better depth of field—focal plane and focus distance are used interchangeable throughout), along the line 8 and along the line 9. One group of cameras, 2, 4, and 6 are focused along the focal plane 8, while the second group of cameras 1, 3, and 5 are focused along the focus distance 9. This allows for the two groups to gather image data of the patient 10 along the vertical length 7 of the patient 10. By use of the two different focal planes 8 and 9, images can be generated of higher quality along the entire image length, than if just taken with a single focal plane.

In certain embodiments, a user can identify the number of images required around the 360 degree view. For example, an image may be captured ever 1, 2, 3, 4, 5, 10, or 15 degrees (and all numbers in between), so as to accurately and fully capture each lesions or other morpholog from a large number of angles. Appropriate sensors and devices can accurately track the position of the cameras to systematically take the images at the predetermined radian around the circumference. Furthermore, the pinion and track can accurately and reproducibly move the sensors or boom along a pre-determined path to allow for reproducible images taken as one or more points around a patient. For example accurate and short movements of between 0 and 15 degrees can be made, with all degrees in-between, for capturing images.

In the second embodiment (single plane of focus) through the use of a multiplicity (five or more) of cameras with very small imaging sensors (around 1" or smaller) with image stitching but without image stacking can yield slightly less depth of field but still with much higher depth of field (because of the small size of the sensors) than typical large sensors used by other researchers.

It is preferable in further embodiments to combine appropriately sized sensors with multiple planes of focus in order to create the greatest detail of the body.

Figure 2:
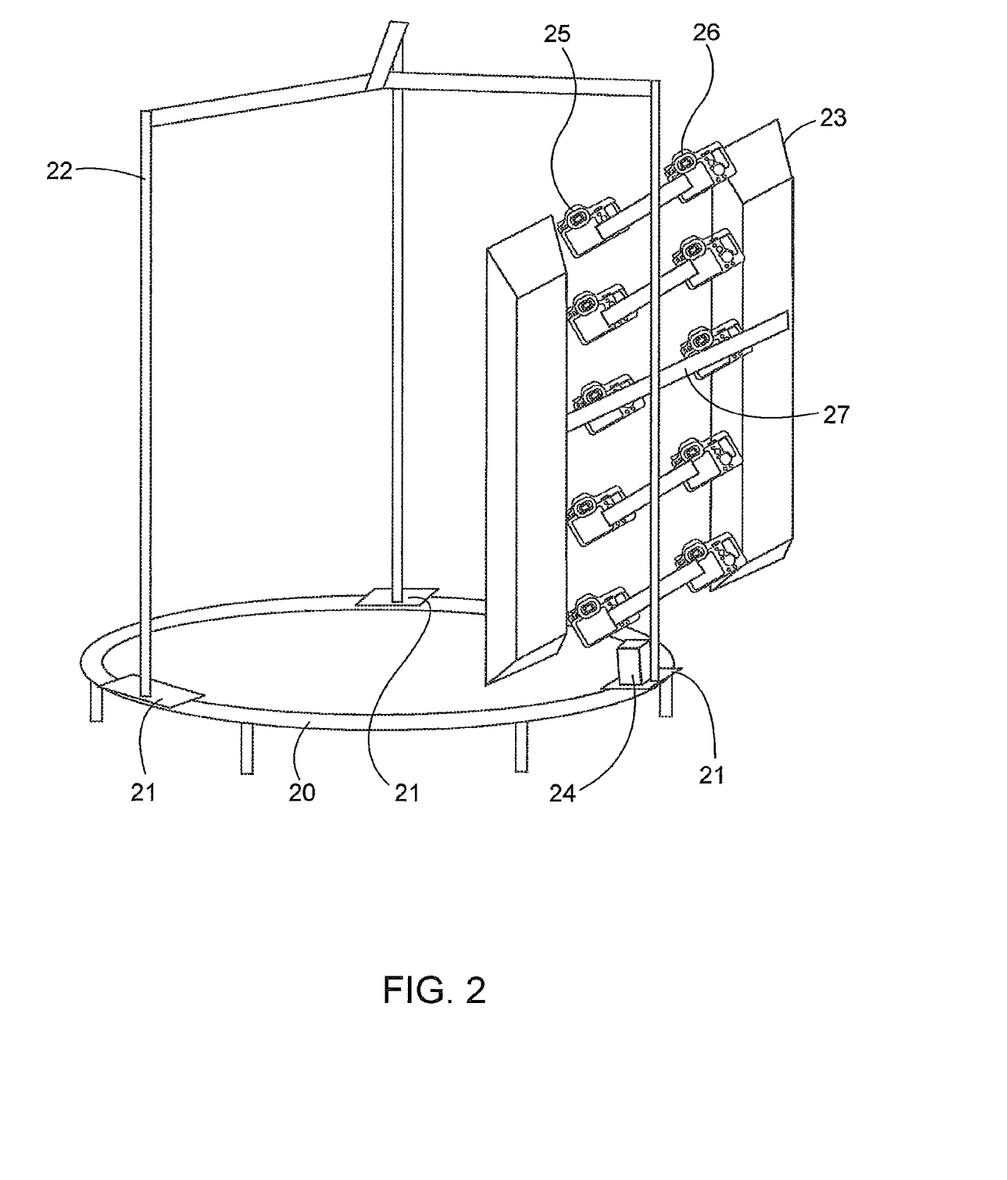
FIG. 2 depicts the scanning device mounted on a steel carriages that moves around on a stationary steel rail system.

FIG. 2 depicts an embodiment of a structure for moving a group of cameras in a rotary fashion around a patient in a consistent manner. Having consistent, reproducible movement allows for images to be compared from a time 1 to a time X. In order to move the entire structure of the device around the subject in standing position, a round stationary rail system and at least one moving carriages will be used. The round stationary rail system will sit on a round stationary ring 20 of the same center diameter. Either inside or outside surface of the ring will be geared (with gear teeth) (See FIG. 6 for example of gearing). The light weight structure of the device will move around the subject on the carriages 21, and moved by a motor 24. The stationary ring 20 allows for movement in a reliable and reproducible manner to allow the carriages 21 to rotate a known distance per movement of the motor. This allows the attached structure 22 to move in a predictable manner. Attached to at least one vertical pole of the structure 22 is a camera tree 27. The tree 27 comprises two lights 23 positioned on either side of at least one group of cameras. Depicted at two groups of cameras, group 25, and group 26, each group comprising five cameras aligned in a vertical manner. An encoder installed on one the carriages 21 with its shaft going through a carriage 21 and connecting with the pinion gears (See FIG. 6) on the aforementioned stationary ring 20 by means a pinion will provide exact position information to a microprocessor that can trigger individual cameras 25 and 26 at prescribed angles around the subject.

For example, a series of images is intended to be taken at every 15 degrees around a patient. Starting at position one, images are taken, the motor rotates a known amount to rotate the structure 15 degrees and a second set of images are taken, the motor rotates again a known distance to 30 degrees and repeats the process until the entire body, or the section to be imaged is completed.

The structure can also be aligned in a horizontal manner and utilized with a person in a lying or recumbent position. In order to move the entire structure of the device around the subject in recumbent position on a long bed, two half round stationary rail systems will be placed above and on either ends of the bed. Either inside or outside surface of the half rings will be geared (with gear teeth). The light weight boom/tree 27 will move around the subject on two carriages 21, on each half ring. Encoders installed on the carriages 21 with its shaft going through a carriage 21 and connecting with the gears on the aforementioned stationary ring by means a pinion will provide exact position information to a microprocessor that can trigger individual cameras 25 and 26 at prescribed angles around the subject.

To move the entire structure of the device around the subject in recumbent position on a long bed, two half round stationary rail systems will be placed above and on either ends of the bed. Either inside or outside surface of the half rings will be geared (with gear teeth). The light weight boom will move around the subject on two carriages (FIG. 10), on each half ring. Encoders installed on the carriages with its shaft going through a carriage and connecting with the gears on the aforementioned stationary ring by means a pinion will provide exact position information to a microprocessor that can trigger individual cameras at prescribed angles around the subject.

Figure 3:
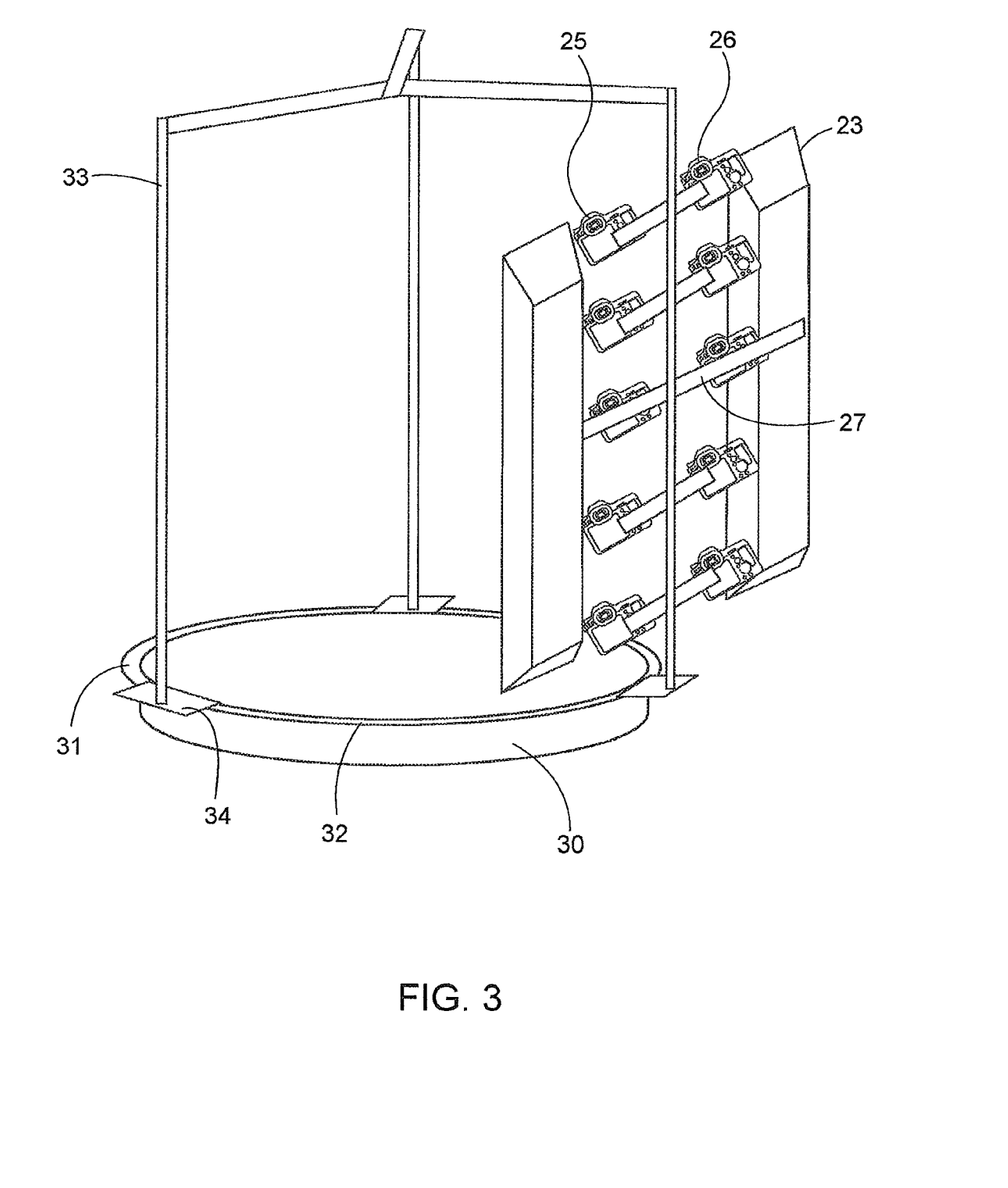
FIG. 3 depicts the scanning the device on an outer ring of a large ball bearing that moves around on a stationary inner ring of the bearing and which in turn the inner ring is affixed on top of a large stationary ring.

In another embodiment the subject will be placed in standing position. The cameras will be installed on a ring (e.g. 3' radius ring) 30. The light sources will be installed on a placed on a structure 33 on the same ring 30 protruding up and down to evenly light the subject. Lights 23 are positioned on a tree 27 with camera groups 25 and 26 positioned between two lights 23. The structure 33 is positioned on a carriage 34, wherein the carriage rotates around the ring 30 on ball bearings 31 and 32. The subject will stand on a pedestal in the middle of the ring. The cameras 25 and 26 will capture images from a variety of angles and focus distances, as the robotics system moves the ring 30 from the lower extremity to upper extremity of the subject covering images from the entire body. Indeed the tree 27 can move both vertically and rotationally. Preferably, the tree 27 rotates with the structure 33 to capture images with the camera groups 25 and 26. Images can be taken in a small angular window or along a 360 degree path around a central patient.

Figure 11:
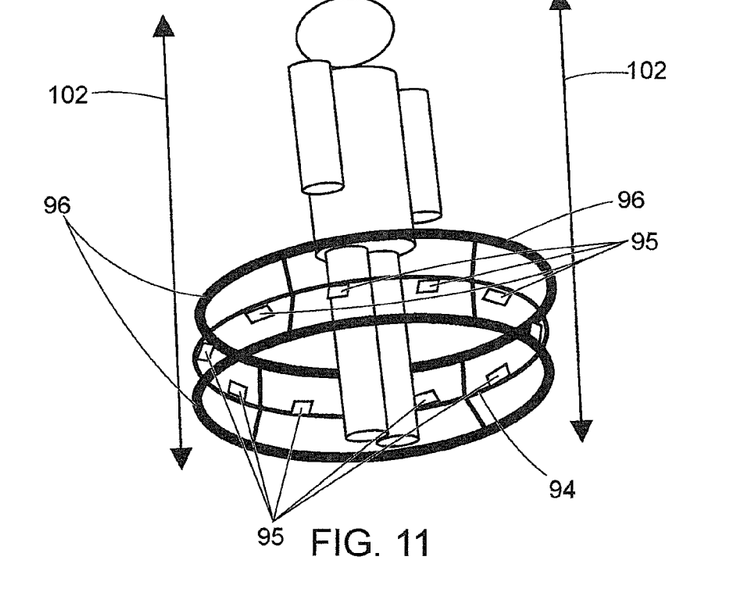
FIG. 11 depicts a patient within a circular structure with a moving ring comprising cameras and light sources.

In another embodiment the subject will be placed in a standing position. The cameras will be installed on a ring (e.g. 3' radius ring) (FIG. 11). The light sources will be installed on the same ring protruding up and down to evenly light the subject. The subject will stand on a pedestal in the middle of the ring. The cameras will capture images as the robotics system moves the ring from the lower extremity to upper extremity of the subject covering images from the entire body.

Figure 12:
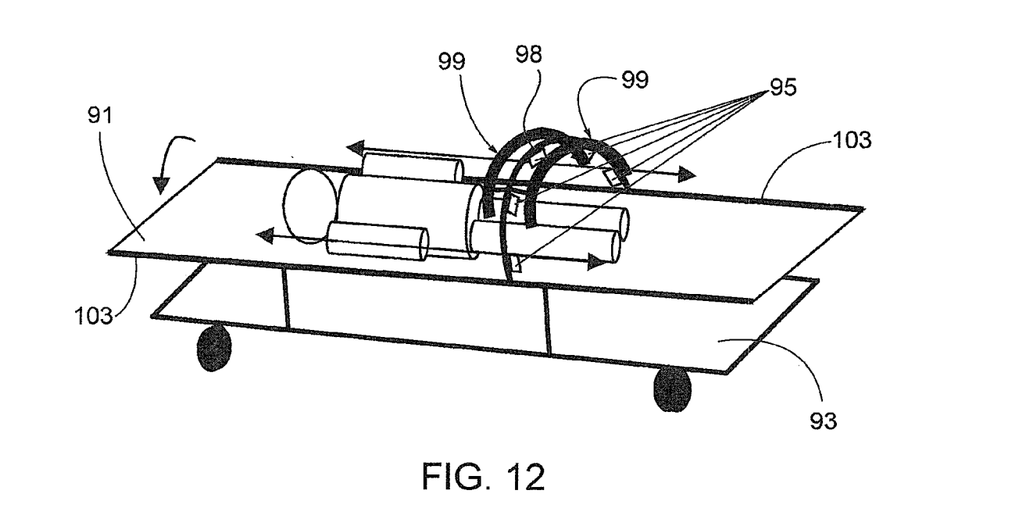
FIG. 12 depicts a patient on a cart device with cameras mounted on a curved rail.

In another embodiment the subject will be placed in a recumbent position. The cameras will be installed on a half ring (e.g. 3' radius ring) (FIG. 12). The light sources will be installed on the same ring protruding left and right to evenly light the subject. The subject will lay on bed in the middle of the half ring. The cameras will capture images from the subject as the robotics system moves the ring from the lower extremity to upper extremity of the subject covering images from the entire body.

Figure 4:
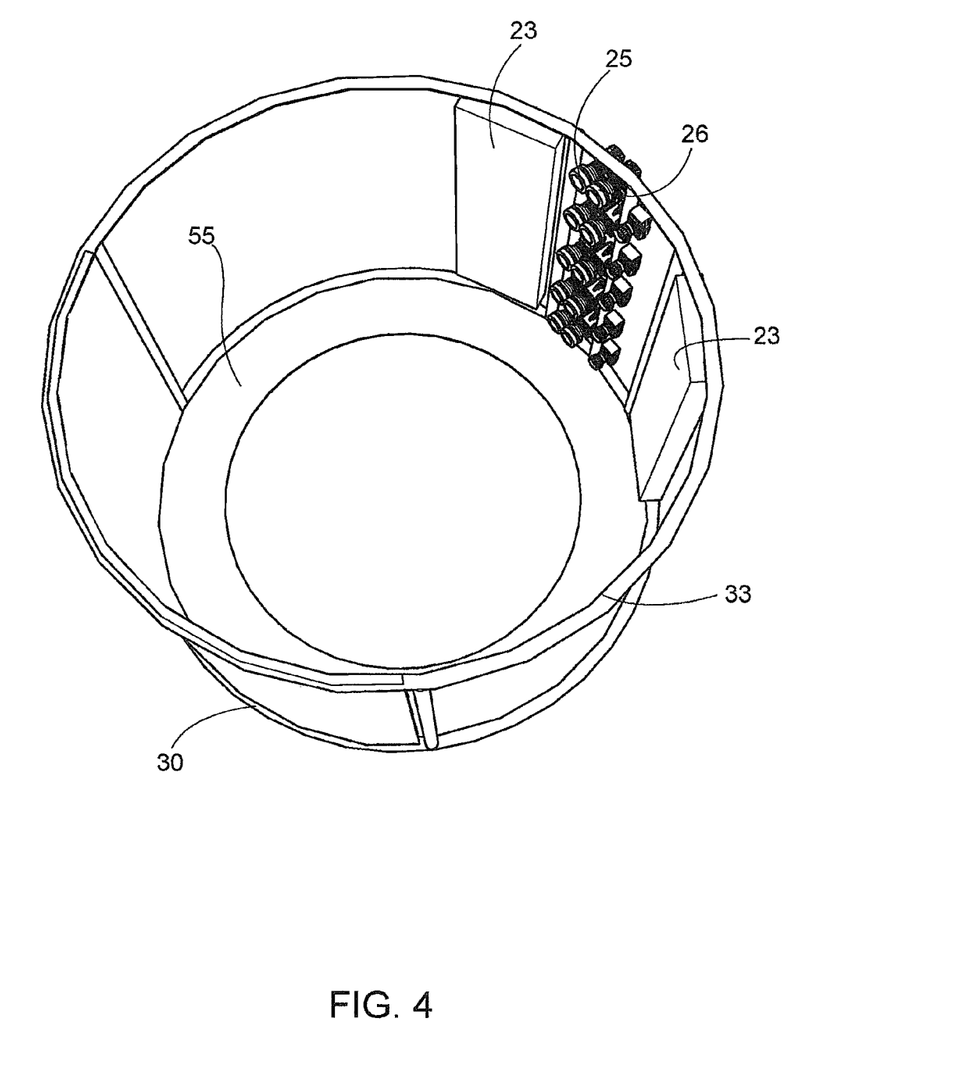
FIG. 4 depicts an embodiment having cameras with different ranges of light frequency sensitivities and light sources with various spectral components, hardware and software.
Figure 5:
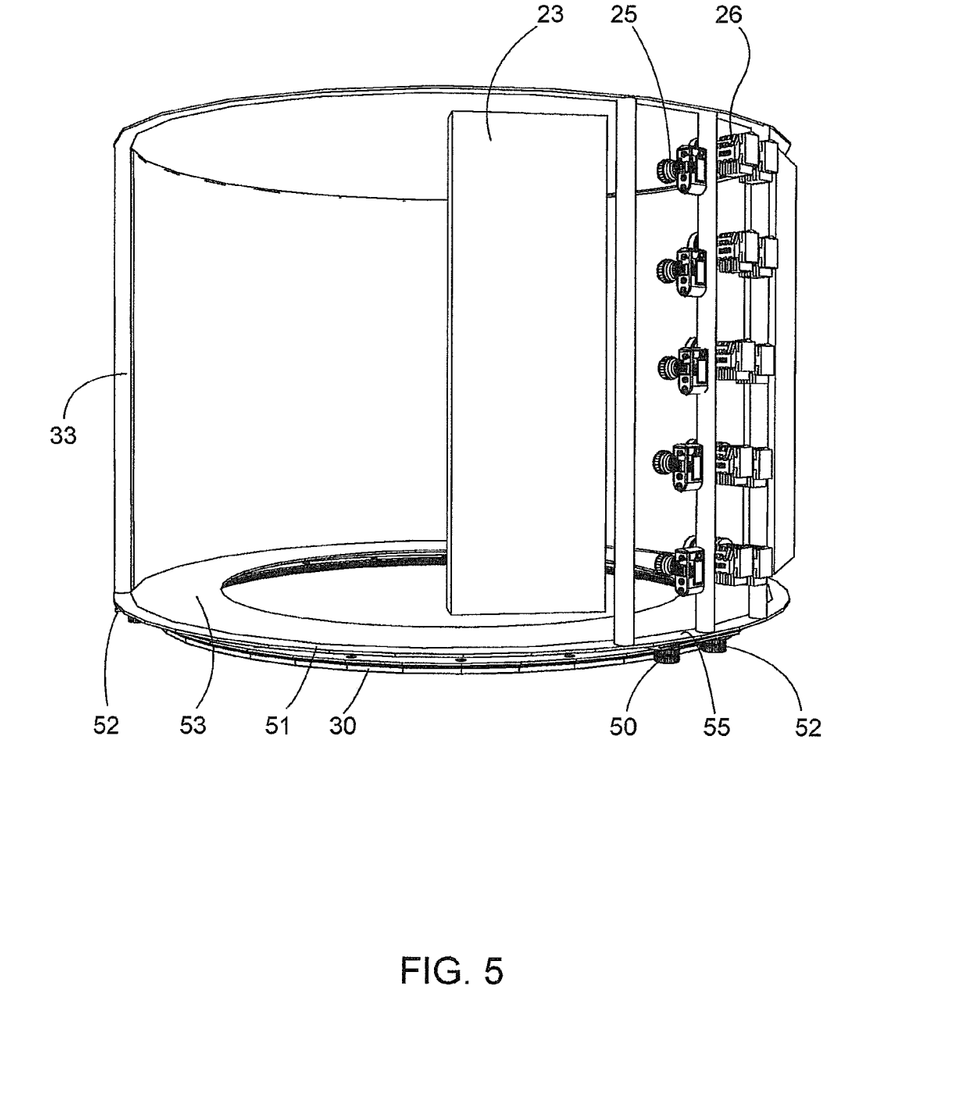
FIG. 5 depicts the scanning device mounted on steel carriages that move around on a stationary steel rail system.
Figure 6:
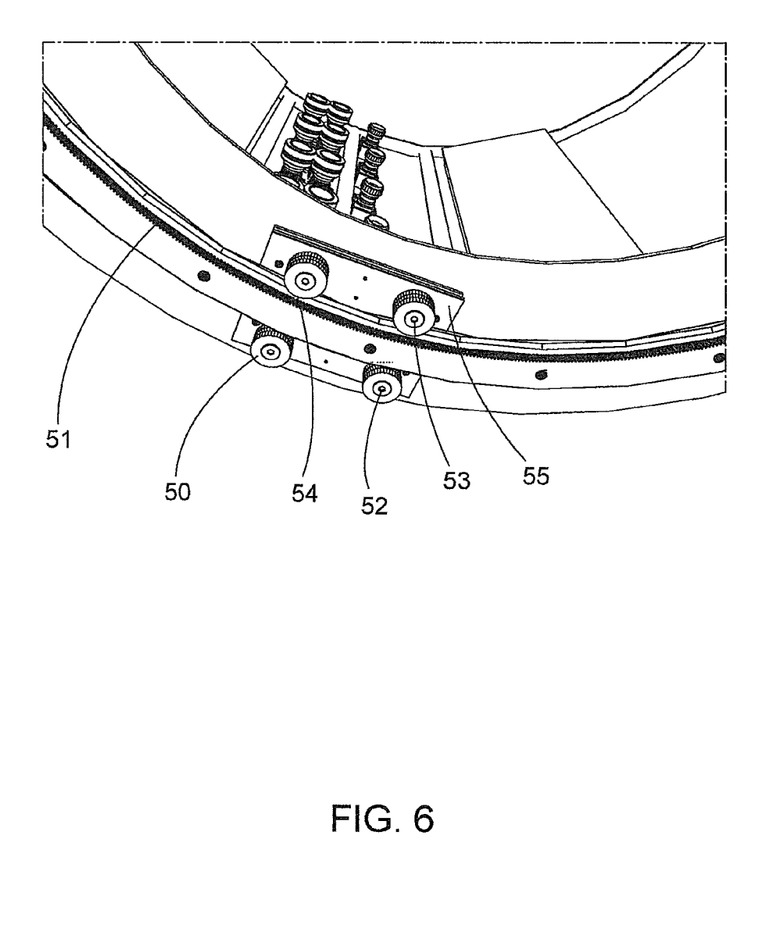
FIG. 6 depicts a round stationary rail system disposed on a round stationary ring of the same center diameter. Either inside or outside surface of the ring will be geared (with gear teeth).

FIGS. 4, 5, and 6 detail further components allowing rotation of a structure 33. For example, FIG. 4 depicts a carriage 55 that rotates around a circular base 30. The lights 23 are depicted surrounding two groups of lights, 25 and 26.

FIG. 5 gives further detail of gears on the carriage 55 to allow for precise rotation of the structure 33 around the circular base 30. Inner and outer gears 50, 52, and 53 contact a track 51, to allow for precise movement and rotation around the circular base 30. The structure 33 contains a light 23 and two groups of cameras 25 and 26.

Finally, FIG. 6 provides greater detail for the track 51, and the inner and outer gears 50, 52, 53, and 54, which rotate on the track 51 to move the carriage 55. The structure 33 is attached to the carriage 55. The track 51 contains notches separated at a pre-defined space, for example a 2 degrees apart, 1 degree apart, 0.5 degrees apart, 0.25 degrees apart, or 0.1 degree apart. This regular spacing allows for repeatable and predictable movement along the track.

In another embodiment the subject will be placed in a recumbent position. The cameras 25 and 26 will be installed on a half ring (e.g. 3' radius ring). The light sources 23 will be installed on the same ring protruding left and right to evenly light the subject. The subject will lay on bed in the middle of the half ring. The cameras 25 and 26 will capture images from the subject as the robotics system moves the ring from the lower extremity to upper extremity of the subject covering images from the entire body.

The stitching of multiple high resolution images can yield an ultra-high resolution images wherein the image can then be utilized by an individual, such as a medical professional, to view and detail the changes in progression of skin diseases, disorders, growths, and the like.

In the preferred embodiment, the invention preserves all the resolution by storing the ultra-high resolution 2D images intact. During the physician's examination, the system simulates 3D by flipping rapidly through a large number of 2D images thereby preserving the entirety of the available resolution. The system will also allow the physician to annotate all areas of interest.

In an additional embodiment, the images will be stored as 3D volumetric data.

In a preferred embodiment, multiple sets of cameras, each set being only sensitive to one spectral domain (such as UV, visible and/or other spectra) will be utilized in order to simultaneously collect data all frequency domains within one rotation of the structure around the subject. Accordingly, in FIG. 1, cameras 1, 3, and 5 may be UV light cameras, while cameras 2, 4, and 6 may be visible light cameras. Other variations or combinations can be combined in any orientation of such cameras.

In another embodiment, the different spectra of light source (e.g. UV, IR) are captured in successive clockwise and counter clockwise movement of the structure around the subject, capturing images of each lesion and other morphologies as illuminated with different spectra of light, from a large number of angles. Thus, as depicted in FIGS. 2 and 3, for example, a first rotation image may capture UV light, a second rotation may capture visible. A further third, or additional rotations may capture additional spectra, such as IR.

Figure 7:
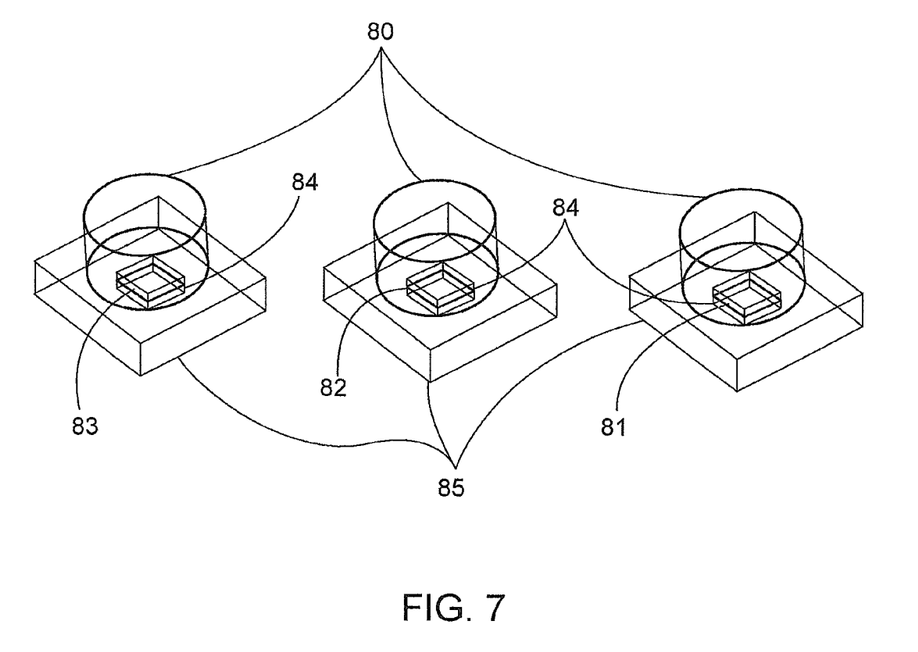
FIG. 7 depicts a set of three cameras and different sensors.

FIG. 7 further details how 3 customized commercial cameras 85 (such as Sony A6500) can be used to capture UV, IR and Visible spectra for each focal distance having a rectangular sensor 84. The visible spectra filter 83 requires no customization or special lenses 80 while in the case of the UV 81 and IR 82 customized cameras the standard visible pass filter 83 on the commercial camera will be replaced with IR 82 or UV 81 pass filters. The UV 81 cameras will be further customized with quartz lenses (each lens depicted as 80), however, for the IR and visible spectra cameras standard glass lens is utilized. In this method one set of cameras 85 consists of six cameras of which three cameras with the afore-mentioned three kinds of filter are focused at a first closer distance and the other three cameras (similarly filtered) cameras are focused at a second the farther distance. The rig will contain five sets of six cameras, where one set will cover the head, one set will cover the upper torso, one set for lower torso, one set upper legs, and the last set for lower leg.

Figure 8:
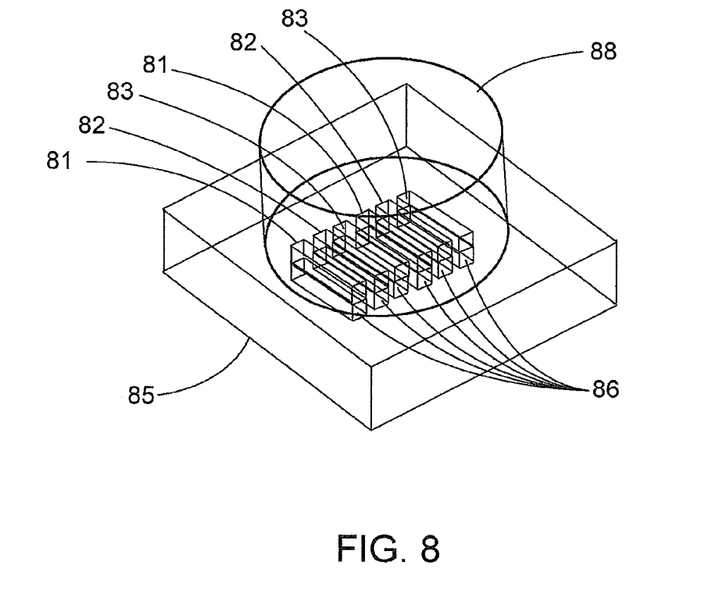
FIG. 8 depicts a camera with line scan sensors, having three different filter options.

FIG. 8 depicts how a set of six cameras can be replaced with one novel camera that features six line-scan sensors 86 with each two having filters for one the three spectra of interest. In other words, two line-scan sensors will have UV pass filters 81, two sensors will have IR pass filters 82 and the last two sets will have visible pass filter 83. The lens 80 in such cameras 85 will be installed at a tilt angle with respect to sensor plane. As a result, the plane of focus will also be at a tilt angle with the plane of sensors. The angle of the tilt will be selected such that the furthest part of the plane of focus is at the same distance as the further part of a typical subject's body from the camera and the closed part of the plane of focus is at the same distance as the nearest part of a typical subject's body. As a result, each lines can sensors 86 will be focused at a different focal distance. Thereby each of the six images rendered from each line-scan sensor after the camera travels over the subject will be focused at a different distance. Stacking the resulting two visible images and the two UV images and two IR images will result into three high depth of field images.

Figure 9:
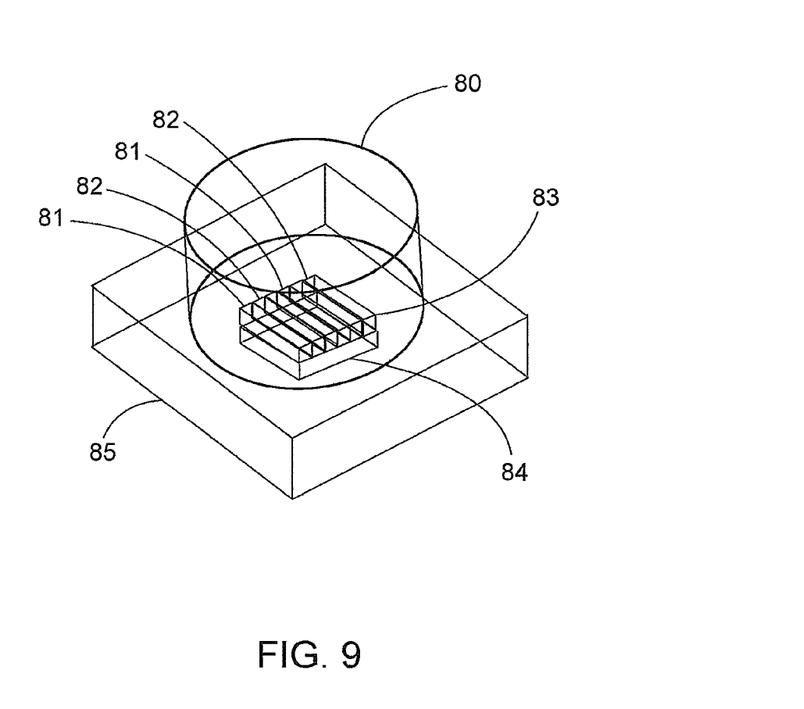
FIG. 9 depicts a camera with three filter options and a rectangular sensor.

FIG. 9 depicts a variation of FIG. 7, where two sets of three cameras can be replaced with one novel camera that features one rectangular sensor 84 and six strips of filters 81, 82, and 83: two strips of UV pass 81, two strips of IR pass 82 and two visible pass filters 83. Accordingly, this allows for a single sensor 84 to be utilized with different filters along a portion of the sensor and to capture a single image from comprising two different views through an IR pass filter 82, a UV pass filter 81, and visible pass filters 83. Furthermore, with the tilted lens, each of the different filters will have a slightly different focus distance, thus allowing greater depth of field images in the tree different filter settings, all captured by the single sensor. Accordingly, use of a camera with the sensor orientation can be exchanged for any of the methods or devices described herein.

Figure 10:
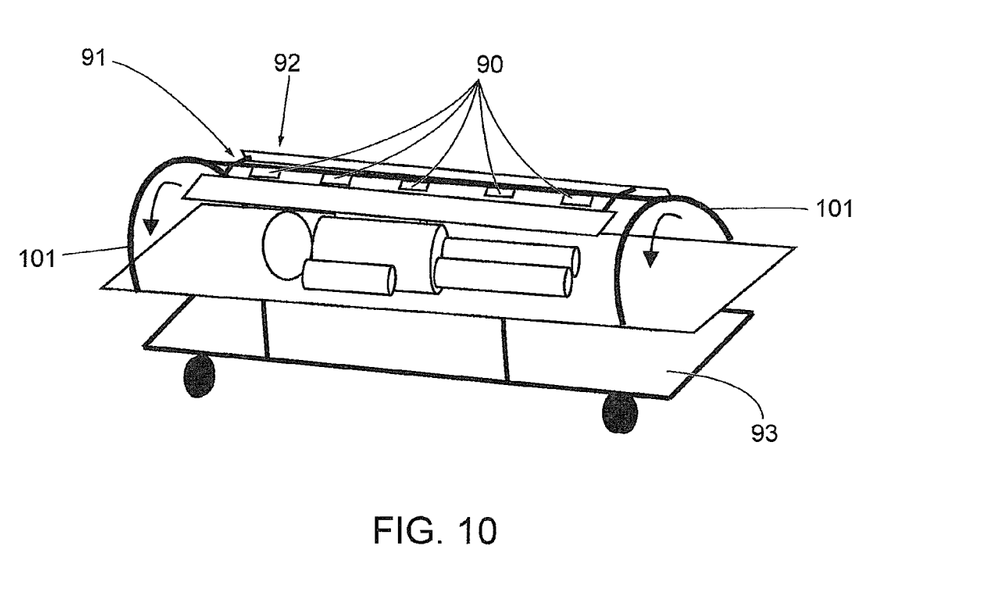
FIG. 10 depicts a patient on a cart device with a rotating boom that rotates about a curved rail.

FIG. 10 depicts a rig configuration on a cart 93 in which the subject is in recumbent position and the five sets of cameras 90 will be installed on boom 91 that will rotate around the subject on two semi-circular rails 101 on the periphery of an imaginary half cylinder centered around the subject. A light source 92 is further provided for consistency of the image.

FIG. 11 depicts a rig configuration in which the subject is on standing position, the camera sets 95 and light sources 96 are installed on six-foot diameter ring 94 that can travel up and down the length of subject on a set of linear rails 102 (two or more rails in one embodiment).

FIG. 12 depicts a rig configuration on a cart 93, in which the subject is on recumbent position, the camera sets 95 and light sources 99 are installed on 6-foot diameter half ring 98 that can travel up and down the length of subject on a set of linear rails 103 (two or more rails in one embodiment). Further, a rotating boom 91 can be utilized to take additional images along the circular path and move the diameter half ring 98 in both a curved fashion and up and down the length of the body of the patient.

Therefore, a preferred embodiment comprises a novel camera and sensor arrangement such as depicted in FIG. 8 that features six line-scan sensors aligned parallel to one another, with each two sensors having filters for one the three spectra of interest resulting in two line-scan sensors will have UV pass filters, two sensors will have IR pass filters and the last two sets will have visible pass filter. The lens in such cameras will be installed at a tilt angle between 0 and 90 degrees, with respect to sensor plane. As a result, the plane of focus will also be at a tilt angle with the plane of sensors. The angle of the tilt will be selected such that the furthest part of the plane of focus is at the same distance as the further part of a typical subject's body from the camera and the closed part of the plane of focus is at the same distance as the nearest part of a typical subject's body. As a result, each lines can sensors will be focused at a different focal distance. Thereby each of the six images rendered from each line-scan sensor after the camera travels over the subject will be focused at a different distance. Stacking the resulting two visible images and the two UV images and two IR images will result into three high depth of field images.

The same lighting system that is incorporated to evenly illuminate the subject may also be used for Phototherapy, albeit at different light intensity level and duration.

Indeed, it is well understood that phototherapy can help certain skin diseases that stem from immune-system including psoriasis, eczema, vitiligo, and cutaneous lymphoma.

Phototherapy is applied in the UV domain, both UVA and UVB. One of the properties of UV spectrum is its ability to suppress immunity, especially presence of T cells in the skin. Therefore, the diseases of the skin that are associated or caused by inflammatory cells, especially T cells, improve with UV exposure.

The device can then be utilized to not just image a person, but the high intensity lights can be programmed to certain wavelengths to provide for appropriate phototherapy in this single device.

Software Examples and Requirements:

Preferred or alternate ways for software deployment: The initial implementation will integrate off-the shelf software for stitching (New House Internet Services BV's PTGui), for stacking (HeliconSoft's Helicon), for presentation (Garden Gnome's object2vr) as well as custom software for robotics control of the structure and image capture. However, the system can be implemented based on other off-the-shelf or custom software components as well (custom software may be necessary for cloud computing).

Ultimately, the system and the medical devices described herein provide for certain advantages over the prior art. In particular, the prior art has difficulty in creating proper color fidelity. Each user and each application will likely result in different light sources. This is due to use of a flash or no flash, ambient lighting changing color temperature (as fluorescent bulbs or halogen bulbs change color temperature over time), and subjective photography. Having any user input into photography ultimately results in images that cannot be compared over time. Therefore, in preferred embodiments, lighting is provided in a consistent manner with specific color indications and a defined CRI. This information can be further gathered in the images to allow for corrections via software, if any light shift is present between uses. For example, replacing bulbs will often modify the color temperature and intensity of light expressed.

For example, a person having melanoma or eczema or psoriasis can be imaged by the device or system as described herein. This image can then be stored and a second and subsequent images taken of the same subject after a predetermined amount of time. The images can then be visually compared to review the change in disease state. For example, in watching certain moles that are at risk for cancer, the images can be zoomed in to compare images from time 1 and time 2 to see if the mole is growing, changing in color, changing in texture, etc. The images provide for a much more accurate depiction of the actual status than written words, as these are merely subjective. Additionally, the system can provide the sizes for the areas of interest for more objective evaluation.

Similarly, visualization of psoriasis or other known skin diseases or disorders can be captured from time 1 to time X, wherein treatment may be provided between Time 1 and Time X, and wherein visual comparison can be made under essentially identical imaging situations. Again, the system can provide the sizes for the areas of interest for more objective evaluation.

The benefit of the device is that the person needs to only spend a short amount of time, i.e. less than 2 minutes including setup and imaging, to get a clear and precise 3D image of the skin. Furthermore, the device is capturing not just visual images, but also UV images to better identify concerning pigmented lesions and nevi. This is because UV imaging can exaggerate skin pigmentation. Consequently, UV imaging can help identify subtle yet concerning pigmentation that may not be best visualized in visible light by photography or with the naked eye. Moreover, it will better define and separate pigmented lesions and nevi from the background. Also, UV imaging can provide the best guidance as to where the skin has been subject to sun induced damage.

What is claimed is:

1. A system for generating wide depth of field and high resolution images comprising:
    two sets of cameras comprising a first camera set and a second camera set;
    a rotatable structure to which the first camera set and the second camera set are mounted for rotating the two sets of cameras around a subject, to produce wide depth of field of images in a high speed manner;
    wherein the first set of camera are focused at the first focus distance and the second set of camera are focused at a second focus distance, the cameras being mounted adjacent to at least one illumination source;
    wherein the rotatable structure is controlled by a program that defines a movement profile along a path of rotation,
    wherein the program moves the first and second sets of cameras around the subject, stops to specific angles of view and obtains images from all the cameras at each stop;
    wherein a subsequent incremental move of the structure will place the second set of cameras at the same angle of view of the subject as the set of first cameras in the next time increment;
    wherein after a set number movements, a full rotation of the structure around the subject is completed;
    wherein the images from the first set of cameras at time increment x are stitched together;
    wherein the images from the second sets of camera at time increment x+1 are stitched together; and
    wherein the resulting image from the stitching operations from the first set of cameras at time increment x and resulting image from stitching operations from the second set of cameras at time increment x+1 are stacked together to create very high resolution and large depth of field image from one angle of view; and by repeating the same process for images obtained at the other angles of views along the path of rotation, the system can produce a plurality of wide depth of field and high resolutions images from all angles of views along a path of rotation.

2. The system of claim 1, wherein the at least one illumination source has the ability to illuminate the subject in various colors of light including UV and white, and wherein a subset of cameras will be UV-sensitive cameras and another subset will be visible light sensitive cameras, to capture multi-spectral, high speed, high depth of field images.

3. The system of claim 1, wherein the illumination source is configured to produce sufficient UV intensity such that the system can be utilized for UVA/UVB phototherapy.

4. The system of claim 1, wherein said two sets of cameras comprise 20 total cameras, comprising a first set of 10 cameras focused at a closer distance and a second set of 10 cameras focused at a further distance, wherein of the first set of 10 cameras, a subset of five cameras is be sensitive to UV light and a second subset of five cameras is sensitive to visible light and wherein of the second set of 10 cameras, a subset of five cameras is sensitive to UV light and a second subset of five cameras is sensitive to visible light.

5. A method of utilizing the images obtained by the system of claim 1 to track and classify a lesion, comprising the steps of:
    determining the actual size of a lesion by utilizing the known positions of the cameras along the path of movement and the known angle of the cameras along the path of movement;
    detecting the boundary of a lesion by computing the boundary multiple times from multiple images of the same lesion and then depending on the mode of device finding the average of the boundaries in diagnostics mode or the union of the resulting boundaries in the screening mode;
    tracking the position of a lesion, by utilizing the actual distances between a lesion and nearby lesions, as well as the actual distances between the lesion and certain body landmarks; and
    classifying the lesion by machine learning based on multiple images of the same lesion.

* * * * *